US012399289B2

(12) United States Patent
Inoue (10) Patent No.: US 12,399,289 B2
(45) Date of Patent: Aug. 26, 2025

(54) RADIATION DETECTOR AND NUCLEAR MEDICINE DIAGNOSTIC APPARATUS

(71) Applicant: CANON MEDICAL SYSTEMS CORPORATION, Otawara (JP)

(72) Inventor: Motohiro Inoue, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 236 days.

(21) Appl. No.: 18/358,376

(22) Filed: Jul. 25, 2023

(65) Prior Publication Data

US 2024/0077627 A1    Mar. 7, 2024

(30) Foreign Application Priority Data

Jul. 26, 2022   (JP) .................. 2022-118372

(51) Int. Cl.
 G01T 1/29    (2006.01)
 A61B 6/03    (2006.01)
 A61B 6/42    (2024.01)
 G01T 1/24    (2006.01)
(52) U.S. Cl.
 CPC ............ G01T 1/2985 (2013.01); A61B 6/037 (2013.01); A61B 6/4241 (2013.01); G01T 1/247 (2013.01); G01T 1/249 (2013.01); G01T 1/248 (2013.01)

(58) Field of Classification Search
 CPC ...... A61B 6/037; A61B 6/4241; A61B 6/4488; G01T 1/247; G01T 1/248; G01T 1/249; G01T 1/2985; G01T 1/17
 See application file for complete search history.

(56) References Cited

U.S. PATENT DOCUMENTS

2017/0322324 A1\*  11/2017  Fu ..................... G01T 1/244
2019/0167214 A1\*  6/2019  Sawada ................ A61B 6/54

FOREIGN PATENT DOCUMENTS

KR         102780860 B1 \*  3/2025  ........... G01R 31/36

\* cited by examiner

*Primary Examiner* — David P Porta
*Assistant Examiner* — Casey Bryant
(74) *Attorney, Agent, or Firm* — Oblon, McClelland, Maier & Neustadt, L.L.P.

(57) ABSTRACT

A radiation detector includes a sensor, an A/D converter, and processing circuitry. The sensor outputs a pulse signal based on incidence of radiation. The A/D converter generates digital data by performing A/D conversion on the pulse signal. The processing circuitry acquires temperature information of the A/D converter and outputs digital data that is compensated based on the temperature information.

10 Claims, 4 Drawing Sheets

RADIATION DETECTOR AND NUCLEAR MEDICINE DIAGNOSTIC APPARATUS

CROSS-REFERENCE TO RELATED APPLICATIONS

This application is based upon and claims the benefit of priority from Japanese Patent Application No. 2022-118372, filed on Jul. 26, 2022, the entire contents of which are incorporated herein by reference.

FIELD

Embodiments described herein relate generally to a radiation detector and a nuclear medicine diagnostic apparatus.

BACKGROUND

Silicon photo multiplier (SiPM) based radiation detectors are known as radiation detectors of nuclear medical diagnosis apparatuses, such as a positron emission computed tomography (PET) apparatus, or radiation diagnostic apparatuses, such as a photon counting computed tomography (PCCT) apparatus.

Analog signal processing in a radiation detector is known as being affected by temperature. For this reason, there has been a problem in that, when a temperature change occurs in the radiation detector due to an effect of unevenness in heat radiation or cooling, a change in surrounding environments, or the like, an output value of energy information or time information changes.

DETAILED DESCRIPTION

A radiation detector according to an embodiment includes a sensor, an A/D converter, and processing circuitry. The sensor outputs a pulse signal based on incidence of radiation. The A/D converter generates digital data by performing A/D conversion on the pulse signal. The processing circuitry acquires temperature information of the A/D converter and outputs digital data that is compensated based on the temperature information.

A radiation detector and a nuclear medicine diagnostic apparatus according to each embodiment will be described with reference to the drawings. In the following description, components having the same or approximately the same functions as those described with respect to the drawings previously presented are denoted with the same reference numerals and are described redundantly only when necessary. Even when the same part is presented, mutual sizes and ratios are sometimes presented differently depending on the drawings. For example, in view of ensuring visibility of the drawings, only main or representative components are sometimes denoted with reference numerals in the description of each drawing and even components having the same or approximately the same functions sometimes are not denoted with reference numerals.

First Embodiment

Figure 1:
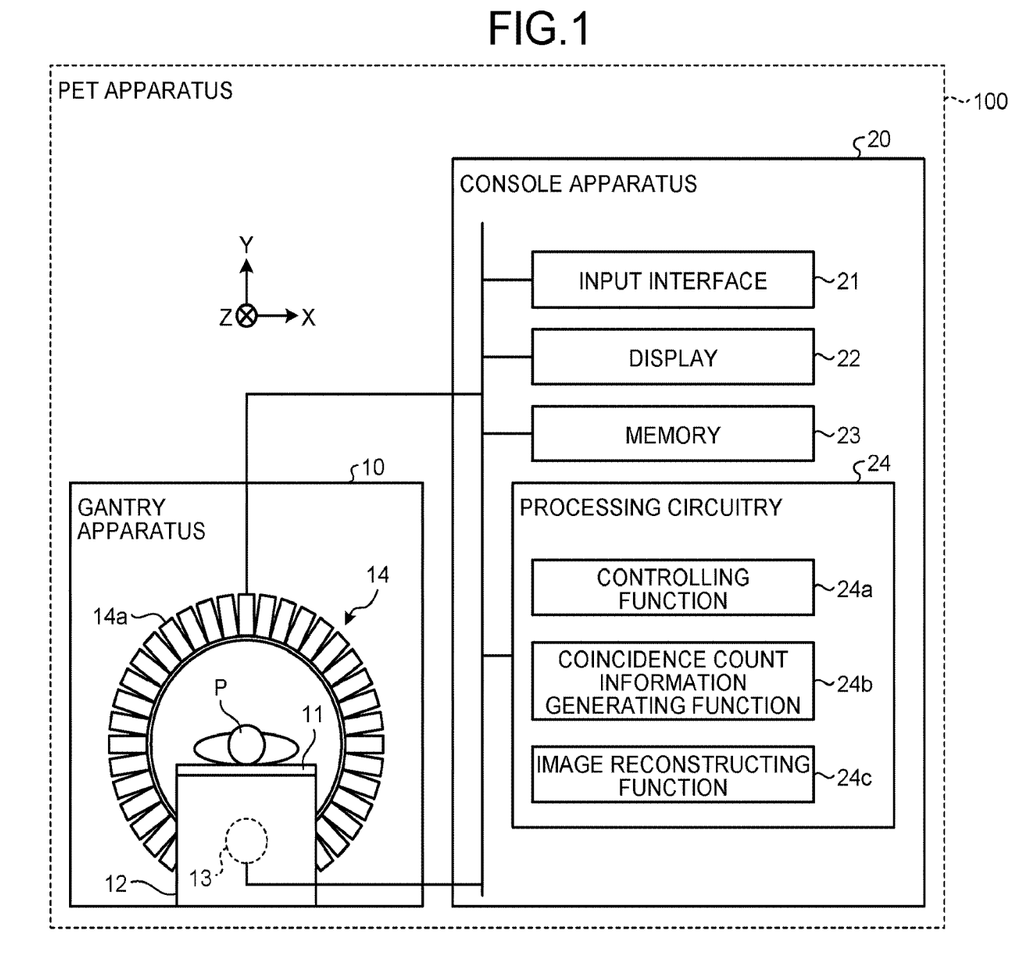
FIG. 1 is a diagram illustrating an example of a configuration of a positron emission computed tomography (PET) apparatus according to an embodiment.

FIG. 1 is a diagram illustrating an example of a configuration of a positron emission computed tomography (PET) apparatus 100 according to a first embodiment. For example, as illustrated in FIG. 1, the PET apparatus 100 includes a gantry apparatus 10 and a console apparatus 20.

The gantry apparatus 10 detects annihilation gamma rays that are emitted because of annihilation of a positron that is emitted from a tracer that is applied to a subject P with an electron and counts the detected annihilation gamma rays, thereby collecting count information. The gantry apparatus 10 has a cylindrical opening that is formed such that the opening penetrates the gantry apparatus 10 in a horizontal direction. The gantry apparatus 10 detects annihilation gamma rays that are emitted from the subject P that is arranged in the opening. Note that, in the following description, the direction along the axis of the cylindrical opening of the gantry apparatus 10 is defined as a Z-axis direction. A horizontal direction orthogonal to the Z-axis direction is defined as an X-axis direction. A vertical direction orthogonal to the Z-axis direction and the X-axis direction is defined as a Y-axis direction.

Specifically, the gantry apparatus includes a tabletop 11, a table 12, a table drive mechanism 13, and a PET detector 14.

The tabletop 11 is a bed on which the subject is laid. For example, the tabletop 11 is formed into a form of a rectangular flat board and is arranged such that its longitudinal direction is parallel with the Z-axis direction.

The table 12 supports the tabletop 11 such that the tabletop 11 is movable in the X-axis direction, the U-axis direction, and the Y-axis direction.

The table drive mechanism 13 is provided inside or outside the table 12 and causes the tabletop 11 that is supported by the table 12 to move. For example, to capture an image of the subject P, the table drive mechanism 13 causes the tabletop 11 with the subject P being laid thereon to move into the opening of the gantry apparatus 10. For example, the table drive mechanism 13 causes the tabletop 11 to move on the table 12 with the position of the table 12 being fixed. Alternatively, for example, the table drive mechanism 13 may include a move base ad cause the tabletop 11 to move together with the table 12 on the move base.

The PET detector 14 detects annihilation gamma rays that are emitted from the subject P. The PET detector 14 generates count information containing detection positions in which the detected annihilation gamma rays are detected, an energy value, and a time of detection and transmits the generated count information to the console apparatus 20.

Specifically, the PET detector 14 includes a plurality of detector units 14a that are arrayed in a form of a ring about the Z-axis such that the detector units 14a surround the opening that is formed in the gantry apparatus 10 and each of the detector units 14a detects an annihilation gamma ray and generates count information.

The detector unit 14a is for example, an anger-type detector employing a photon-counting system and includes a scintillator, a photodetector device and a light guide.

The scintillator converts the annihilation gamma ray that is emitted from the positron in the subject P and that is incident on the scintillator into scintillation light and outputs the scintillation light. For example, the scintillator is formed of scintillator crystals of LaBr3, LYSO, LSO, LGSO, BGO, GAGG, LuAG, or the like, suitable for energy measurement. For example, the scintillator has a two-dimensional array.

The photodetector device detects the scintillation light that is output from the scintillator and converts the scintillation light into an analog signal. The photodetector device consists of, for example, a silicon photomultiplier (SiPM); however, the photodetector device may consist of another photomultiplier tube, such as a photomultiplier (PMT).

The light guide is formed of a plastic material with superior optical transmissivity and transmits the scintillation light that is output from the scintillator to the photodetector device.

The detector unit 14a may be a non-anger-type detector without a light guide in which a scintillator and a photodetector device are optically joined in a pair. Alternatively, for example, the detector unit 14a may be not an indirect-conversion-type detector using a scintillator but a direct-conversion-type detector using a semiconductor, such as CZT, CdTe, Ge, or Si.

Based on an analog signal that is output from the photodetector device, the detector unit 14a generates count information containing a position of detection of an annihilation gamma ray, an energy value, and a time of detection.

For example, the detector unit 14a specifies a plurality of photodetector devices that convert scintillation light into analog signals at the same timing. The detector unit 14a specifies a position in the scintillator where an annihilation gamma ray is incident as a position of detection of the annihilation gamma ray. For example, by performing center-of-gravity computation based on the position of the photodetector device and the intensity of the analog signal, the detector unit 14a specifies the position in the scintillator where the annihilation gamma ray is incident. Alternatively, for example, when the device sizes of the scintillator and the photodetector device correspond to each other, the detector unit 14a may specify the position in the scintillator corresponding to the photodetector device from which an output is obtained as a position in the scintillator where the annihilation gamma ray is incident.

For example, the detector unit 14a performs integral computation on the intensity of the analog signal that is output from the photodetector device, thereby specifying the energy value of the annihilation gamma ray. Alternatively, for example, the detector unit 14a may measure a time (time over threshold (ToT)) in which the intensity of the analog signal that is output from the photodetector device exceeds a threshold that is set in advance and, by performing non-linear correction using the measured time, measure the energy value of the annihilation gamma ray.

For example, the detector unit 14a specifies the time in which the scintillation light is detected by the photodetector device as a time of detection of the annihilation gamma ray. The time of detection may be an absolute time or an elapsed time from the time of start of imaging.

The console apparatus 20 receives various types of operations on the PET apparatus 100 from an operator and controls operations of the PET apparatus 100 according to the received operations. Specifically, the console apparatus 20 includes an input interface 21, a display 22, a memory 23, and a processing circuitry 24. Each unit that the console apparatus 20 includes is connected via a bus. A case where the gantry apparatus 10 and the console apparatus 20 are independent from each other is exemplified here; however, the gantry apparatus 10 may include the console apparatus 20 or part of the components of the console apparatus 20.

The input interface 21 receives various input operations from the operator, converts the received input operations into electric signals, and outputs the electric signals to the processing circuitry 24. For example, the input interface 21 receives operational inputs for setting imaging conditions and a region of interest (ROI) from the operator.

For example, a mouse, a keyboard, a trackball, a switch, a button, a joystick, non-contact input circuitry using an optical sensor, audio input circuitry, a touch pad, a touch panel display, and the like, are usable as appropriate as the input interface 21.

In the first embodiment, the input interface 21 is not limited to one including these physical operational parts. For example, examples of the input interface 21 include an electric signal processing circuitry that receives an electric signal corresponding to an input operation from an external input device that is provided independently of the apparatus and that outputs the electric signal to the processing circuitry 24. The input interface 21 may be provided in the gantry apparatus 10. The input interface 21 may consist of a tablet terminal device capable of radio communication with the console apparatus 20. The input interface 21 is an example of the input unit.

The display 22 displays various types of information. For example, the display 22 outputs a medical image (a PET image) that is generated by the processing circuitry 24 and a graphical user interface (GUI) for receiving various types of operations from the operator. Various freely-selected displays are usable as appropriate as the display 22. For example, a liquid crystal display (LCD), a cathode ray tube (CRT) display, an organic electro luminescence display (OELD), or a plasma display is usable as the display 22.

Note that the display 22 may be provided anywhere in a control room. The display 22 may be provided on the gantry apparatus 10. The display 22 may be a desktop-type one or may consist of a tablet terminal device capable of radio communication with the main unit of the console apparatus 20. At least one projector may be used as the display 22. The display 22 is an example of a display unit.

The memory 23 stores various types of data and programs that are used in the PET apparatus 100. The memory 23 is realized by, for example, a semiconductor memory device, such as a read only memory (ROM), a random access memory (RAM), or a flash memory, a hard disk, or an optical disk. The storage area of the memory 23 may be in the PET apparatus 100 or may be in an external storage device that is connected via a network. The memory 23 is an example of a storage unit.

The processing circuitry 24 controls entire operations of the PET apparatus 100. The processing circuitry 24 includes a processor and a memory, such as a ROM or a RAM, as hardware resources. The processing circuitry 24 executes various types of functions, such as a controlling function 24a, a coincidence count information generating function 24b, and an image reconstructing function 24c, using a processor that executes a program that is loaded in the memory. The processing circuitry 24 is an example of a processor.

In the controlling function 24a, the processing circuitry 24 controls each unit of the gantry apparatus 10 and the console apparatus 20, thereby controlling the entire PET apparatus 100. For example, the processing circuitry 24 controls the table drive mechanism 13 to move the tabletop 11. For example, the processing circuitry 24 controls the PET detector 14 to collect count information and stores the collected count information in the memory 23.

In the coincidence count information generating function 24b, the processing circuitry 24 generates coincidence count information using the count information that is collected. Specifically, the processing circuitry 24 refers to the count information that is stored in the memory 23 and, based on the times of detection of the respective sets of count information, specifies a pair of sets of count information obtained by counting annihilation gamma rays approximately concurrently. The processing circuitry 24 generates coincidence count information in which the specified sets of count information in a pair are associated with each other and stores the generated coincidence count information in the memory 23. Based on a plurality of sets of time information that are acquired by the detector units 14a, the processing circuitry 24 corrects a difference in time information between the detector unit 14a serving as a reference and the detector unit 14a that is another detector unit.

In the image reconstructing function 24c, the processing circuitry 24 reconstructs a PET image based on the coincidence count information that is generated by the coincidence count information generating function 24b. Specifically, the processing circuitry 24 reads the coincidence count information that is stored in the memory 23 and performs back projection processing using the read coincidence count information as projection data, thereby reconstructing a PET image. The processing circuitry 24 stores the reconstructed PET image in the memory 23.

Each of the functions 24a to 24c is not limited to the case where the functions are realized by a single set of processing circuitry. A plurality of independent processors may be combined to configure the processing circuitry 24 and the processors may execute programs, respectively, thereby implementing the respective functions 24a to 24c. The functions 24a to 24c may be distributed or integrated as appropriate to a plurality of sets of processing circuitry or into a single processing circuitry.

Note that the console apparatus 20 is described as one that executes the functions using a single console; however, different consoles may execute the functions. For example, the console apparatus 20 may have the functions of the processing circuitry 24, such as the coincidence count information generating function 24b and the image reconstructing function 24c, in a distributed manner.

Part of or all the processing circuitry 24 is not limited to the case where it is included in the console apparatus 20 and part of or all the processing circuitry 24 may be included in an integration server that collectively performs processing on data that is acquired in a plurality of medical image diagnostic apparatuses.

At least one of a process of generating coincidence count information and a process of reconstructing a PET image may be performed by any one of the console apparatus 20 and an external work station. Both the console apparatus 20 and the work station may perform the processes concurrently. For example, a computer including a processor that implements functions corresponding to the respective processes and a memory, such as a ROM or a RAM, as hardware resources is usable as appropriate as the work station.

A configuration example of the PET apparatus 100 according to the first embodiment has been described. Under such a configuration, as described above, the PET apparatus 100 specifies a pair of sets of count information obtained by counting annihilation gamma rays approximately concurrently from the count information on annihilation gamma rays that are detected by the detector units 14a and, based on the coincidence count information in which the specified sets of count information in a pair are associated with each other, generates a PET image.

In the PET apparatus 100 described above, analog signal processing in the PET detector 14 is affected by temperature. There is a possibility that a temperature change in the PET detector 14 lowers the timing of detection and an energy resolution. For this reason, it is important to put the PET detector 14 in a stable temperature environment.

Photodetector devices (photoelectric conversion devices), such as a SiPM, and A/D conversion devices are known as particularly tending to be affected by temperature. More specifically, as for the effect of temperature on the PET detector 14, the effect on the photoelectric conversion device is dominant. For this reason, in general, the voltage to be applied is varied according to a change in the temperature of the photoelectric conversion device and a compensation is made in order to obtain stable energy information. Specifically, a parameter is adjusted in order to perform appropriate voltage control based on the result of actual measurement of the temperature of the photoelectric conversion device.

There is however a risk that only the temperature of the A/D conversion device changes in the case where an abrupt temperature change occurs in the PET detector 14, or the like. In this case, there is a problem in that, when the temperature of the A/D conversion device changes, output values of the energy information and the time information change abruptly according to a resolution of the A/D conversion device.

Thus, the PET detector 14 according to the first embodiment is configured to output digital data on which a temperature compensation based on the temperature of an A/D converter 145 is made. The PET detector 14 is an example of a radiation detector.

A temperature compensation further based on the temperature of the photoelectric conversion device in addition to the temperature of the A/D converter 145 can be made.

Figure 2:
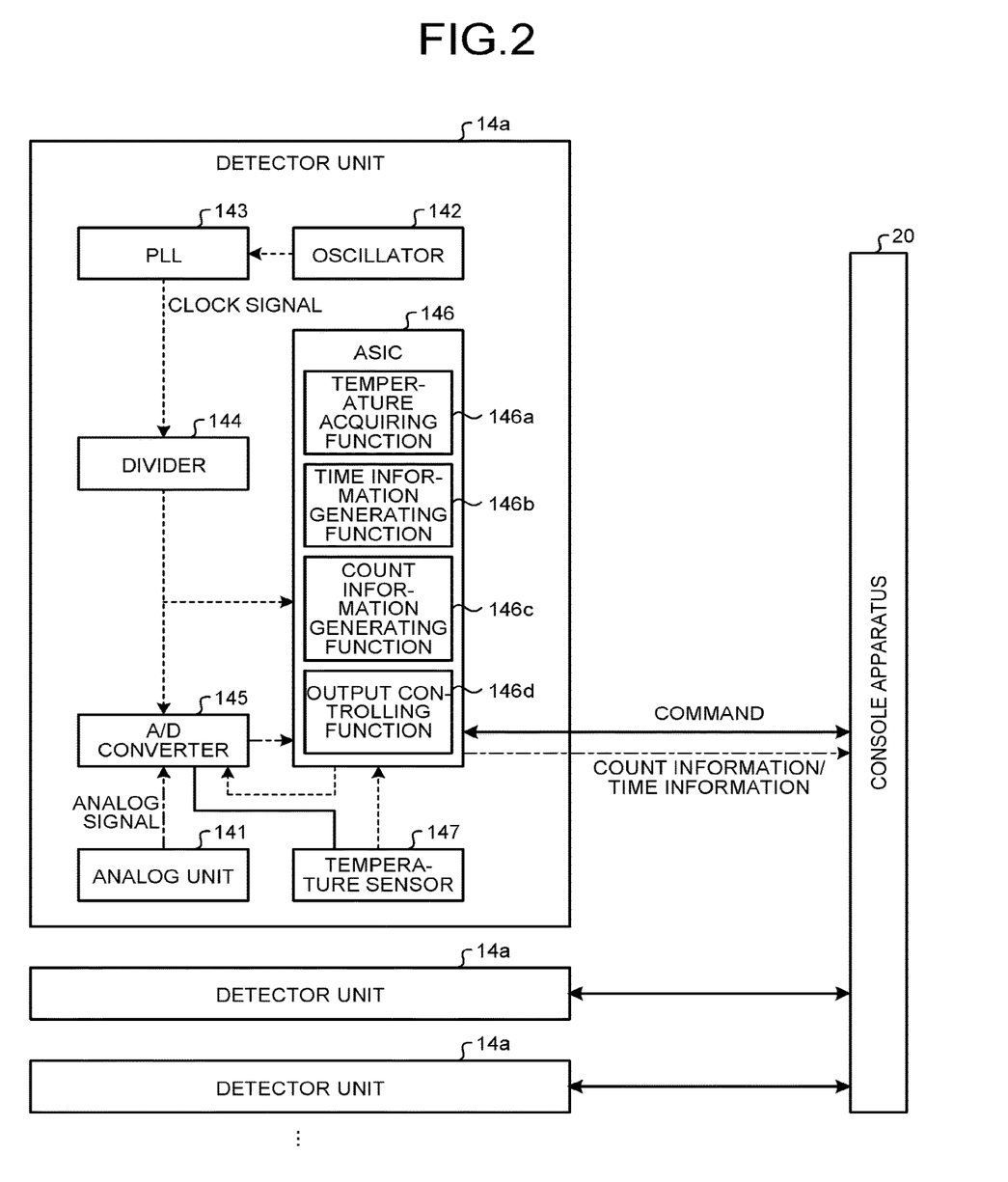
FIG. 2 is a diagram illustrating an example of a detector unit according to the embodiment.

The configuration example of the PET detector 14 according to the first embodiment will be described more in detail. FIG. 2 is a diagram illustrating a configuration example of the detector unit 14a according to the first embodiment.

In the PET detector 14, each of the detector units 14a includes an analog unit 141, a data acquisition system (DAS) and a temperature sensor 147. For example, the DAS includes an oscillator 142, a phase locked loop (PLL) 143, a divider 144, the A/D converter 145, and application specific integrated circuit (ASIC) 146.

In the PET detector 14, event data is collected in each block containing at least one single detector unit 14a. In the first embodiment, the case where event data is collected in each detector unit 14a will be exemplified.

The analog unit 141 outputs a pulse signal based on incidence of radiation. Specifically, the analog unit 141 detects an analog signal based on the result of detection of a gamma ray. Specifically, the analog unit 141 includes the scintillator and the photodetector device (photoelectric conversion device) described above, converts an annihilation gamma ray that is emitted from a positron in the subject P and is incident into scintillation light, converts the scintillation light into an analog pulse signal, and outputs the analog pulse signal. The pulse signal is referred to as a detection signal below. The analog unit 141 is an example of a sensor unit (sensor).

The oscillator 142 generates a clock signal. For example, the oscillator 142 is realized using circuitry using a built-in oscillator, such as a crystal oscillator.

The phase locked loop (PLL) 143 converts a clock signal that is generated by the oscillator 142 into a clock signal of a pre-determined frequency and outputs the clock signal.

The divider 144 divides the clock signal that is output from the PLL 143 to the A/D converter 145 and the ASIC 146.

The A/D converter 145 performs A/D conversion on the detection signal from the analog unit 141, thereby generating digital data. The A/D converter 145 generates digital data (event data) per event. Specifically, on receiving an input of the detection signal that is analog data, the A/D converter 145 converts the detection signal into digital data. The digital data contains the position of detection of annihilation radiation (for example, identification information of the detector unit 14a, the photoelectric conversion device or the scintillator), the energy value (for example, the intensity of the detection signal), and the time of detection (for example, the absolute time or the elapsed time from the start of imaging). Based on the clock signal that is generated by the oscillator 142, the A/D converter 145 measures a time when the intensity of the analog detection signal that is detected by the analog unit 141 exceeds the given threshold and converts the time into a digital signal, thereby generating the time information. The A/D converter 145 is an example of an A/D converter.

The ASIC 146 is configured to be able to execute various types of functions, such as a temperature acquiring function 146a, a time information generating function 146b, a count information generating function 146c, and an output controlling function 146d.

In the temperature acquiring function 146a, the ASIC 146 acquires temperature information from the temperature sensor 147. The ASIC 146 that realizes the temperature acquiring function 146a is an example of an acquisition unit.

For example, the temperature information is information presenting the value of the temperature of the A/D converter 145 or the vicinity of the A/D converter 145 that is measured by the temperature sensor 147. Alternatively, for example, the temperature information may be information presenting a section of the temperature of the A/D converter 145 or the vicinity of the A/D converter 145. The section of temperature can be set, for example, according to a threshold described below.

In the time information generating function 146b, the ASIC 146 acquires the time information (digital data) that is generated by the A/D converter 145 according to a synchronization signal that is generated by a synchronization signal generator. The ASIC 146 transmits the acquired time information to the console apparatus 20.

For example, the synchronization signal generator may be the scintillator included in the analog unit 141. The synchronization signal is a gamma ray that is generated by self-decay of the scintillator. For example, the ASIC 146 acquires the time information in response to occurrence of a gamma ray because of self-decay of the scintillator. For example, the synchronization signal generator may be a gamma ray source that is arranged in the opening of the gantry apparatus 10. The synchronization signal may be a gamma ray that is emitted from the gamma ray. For example, the synchronization signal generator may be the controlling function 24a of the console apparatus 20. The synchronization signal may be a command that is transmitted from the controlling function 24a.

In the count information generating function 146c, based on the analog detection signal that is output from the analog unit 141 and the time information that is generated by the A/D converter 145, the ASIC 146 generates the count information (digital data) containing the position of detection of the annihilation gamma ray, the energy value, and the time of detection. The ASIC 146 transmits the generated count information to the console apparatus 20.

In the output controlling function 146d, the ASIC 146 performs output control of outputting the digital data that is compensated based on the temperature information that is acquired from the temperature sensor 147. Details of the output control based on the temperature information will be described below. The ASIC 146 that realizes the output controlling function 146d is an example of an output controller.

The example using the ASIC 146 has been described; however, the processing circuitry is not limited thereto. For example, another set of processing circuitry that is realized by, instead of the ASIC 146, a processor, such as a central processing unit (CPU), a graphics processing unit (GPU), a field programmable gate array (FPGA), a simple programmable logic device (SPLD), or a complex programmable logic device (CPLD), may be used.

The temperature sensor 147 includes at least a sensor capable of measuring the temperature of the A/D converter 145. The temperature sensor 147 may be a sensor capable of measuring a temperature of a board on which the A/D converter 145 is mounted as the temperature of the A/D converter 145. The temperature sensor 147 may further include a sensor capable of measuring a temperature of a SiPM (photoelectric conversion device). For example, a thermistor is used as the temperature sensor 147, and another sensor capable of measuring a temperature, such as a thermocouple or a radiation thermometer, may be used.

The temperature compensation will be described here more in details with reference to the accompanying drawings. Each of FIGS. 3 to 5 is a diagram for describing temperature compensation according to the first embodiment.

In the output controlling function 146d, the ASIC 146 performs output control of setting a threshold for the pulse signal from the analog unit 141 based on the temperature information. In the first embodiment, the threshold for the pulse signal from the analog unit 141 is a threshold for energy measurement on the pulse signal.

Figure 3:
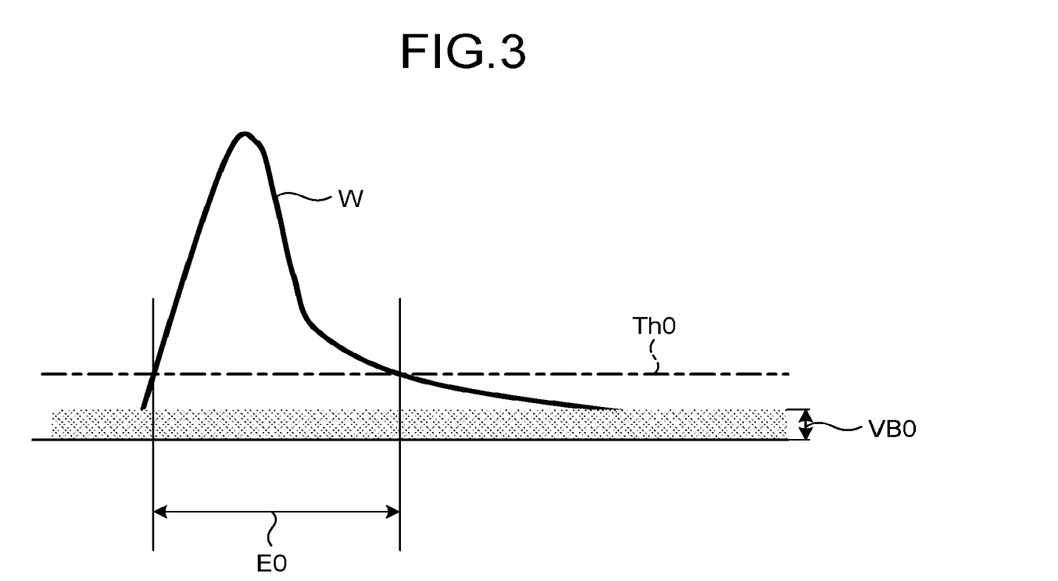
FIG. 3 is a diagram for describing temperature compensation according to the embodiment.

FIG. 3 exemplifies an analog waveform W of the detection signal from the A/D converter 145 in a standard temperature environment. When the temperature information is information presenting the standard temperature environment, in the output controlling function 146d, the ASIC 146 performs output control of setting a threshold Th0 for the detection signal from the analog unit 141. The threshold Th0 is determined in advance according to a base voltage VB0 of the A/D converter 145. The description will be continued, assuming that energy information E0 is obtained as a result of A/D conversion on the detection signal of the analog waveform W using the threshold Th0.

Figure 4:
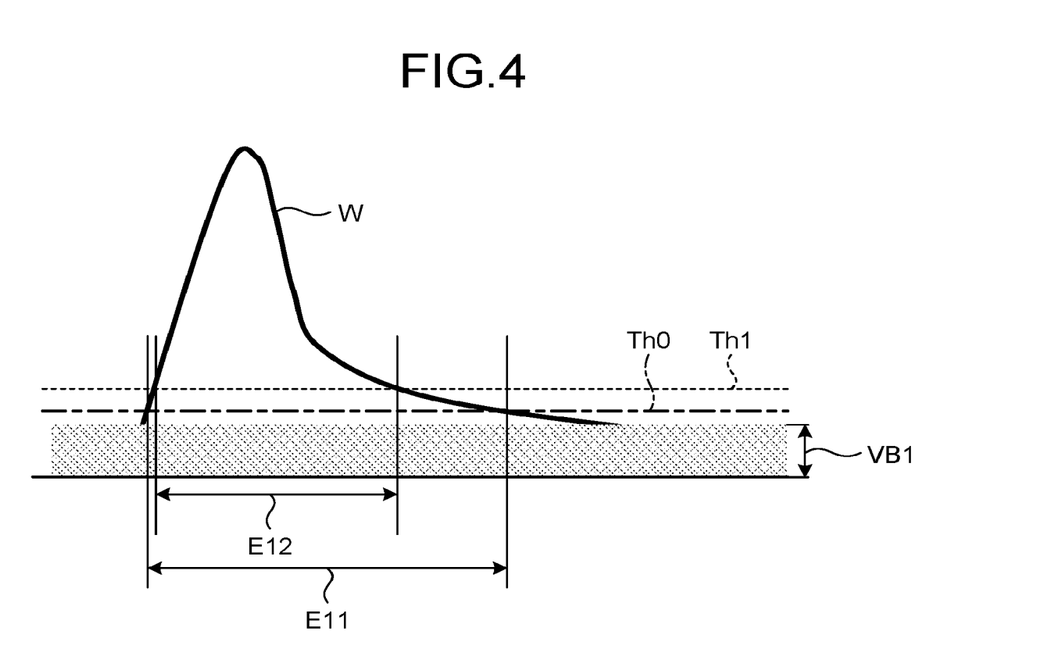
FIG. 4 is a diagram for describing the temperature compensation according to the embodiment.
Figure 5:
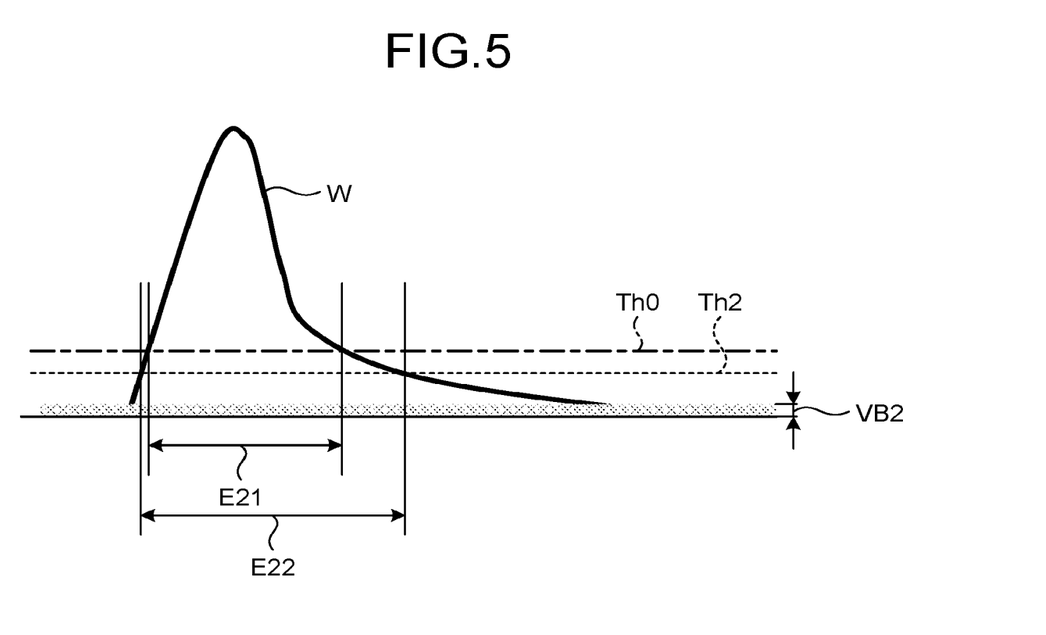
FIG. 5 is a diagram for describing the temperature compensation according to the embodiment.

FIG. 4 exemplifies an analog waveform W of the detection signal from the A/D converter 145 at the time when only the temperature of the A/D converter 145 increases. The base voltage of the A/D converter 145 at that time is a voltage VB1 that is higher than the voltage VB0 in association with the increase in temperature. For this reason, as illustrated in FIG. 4, with the increase of the base voltage of the A/D converter 145, the analog waveform W of the detection signal from the A/D converter 145 transitions to a higher value (upward in FIG. 3 and FIG. 4). Accordingly, the A/D conversion using the threshold Th0 corresponding to the standard temperature environment generates energy information E11 higher than the energy information E0.

As described above, because the temperature change occurring in the A/D converter 145 causes a change in the output value of the energy information, the output control based on the temperature information according to the first embodiment changes the threshold that is set for the analog detection signal for performing A/D conversion according to the temperature information.

Specifically, when the temperature information is information presenting an environment at a temperature higher than that of the standard temperature environment, in the output controlling function 146*d*, the ASIC 146 performs output control of setting a threshold Th1 for the detection signal from the analog unit 141. In other words, when the temperature information is information presenting an environment at a temperature higher than that of the standard temperature environment, the ASIC 146 changes the threshold that is set for the analog detection signal for performing A/D conversion from the threshold Th0 corresponding to the standard temperature environment to the threshold Th1 corresponding to a high-temperature environment. The threshold Th1 is a value that is determined in advance according to the base voltage VB1 of the A/D converter 145 or a range thereof and is higher than the threshold Th0.

According to the A/D conversion using the threshold Th1 corresponding to the high-temperature environment, energy information E12 lower than the energy information E11 is generated. It is thus possible to inhibit an increase in the output value of the energy information resulting from the temperature increase occurring in the A/D converter 145.

FIG. 5 exemplifies an analog waveform W at the time when only the temperature of the A/D converter 145 lowers. The base voltage of the A/D converter 145 at that time is a voltage VB2 that is lower than the voltage VB0 in association with the decrease in temperature. For this reason, as illustrated in FIG. 5, in association with the decrease of the base voltage of the A/D converter 145, the analog waveform W of the detection signal from the A/D converter 145 transitions to a lower value (downward in FIG. 3 and FIG. 5). Accordingly, the A/D conversion using the threshold Th0 corresponding to the standard temperature environment generates energy information E21 lower than the energy information E0.

Thus, in the output control based on the temperature information according to the first embodiment, when the temperature information is information presenting an environment at a temperature lower than that of the standard temperature environment, in the output controlling function 146*d*, the ASIC 146 performs output control of setting a threshold Th2 for the detection signal from the analog unit 141. In other words, when the temperature information is information presenting an environment at a temperature lower than that of the standard temperature environment, the ASIC 146 changes the threshold that is set for the analog detection signal for performing A/D conversion from the threshold Th0 corresponding to the standard temperature environment to the threshold Th2 corresponding to a low-temperature environment. The threshold Th2 is a value that is determined in advance according to the base voltage VB2 of the A/D converter 145 or a range thereof and is lower than the threshold Th0.

According to the A/D conversion using the threshold Th2 corresponding to the low-temperature environment, energy information E22 higher than the energy information E21 is generated. It is thus possible to inhibit a decrease in the output value of the energy information resulting from the temperature decrease occurring in the A/D converter 145.

A flow of the output control based on the temperature information according to the first embodiment will be described more in detail with reference to the accompanying drawings.

Figure 6:
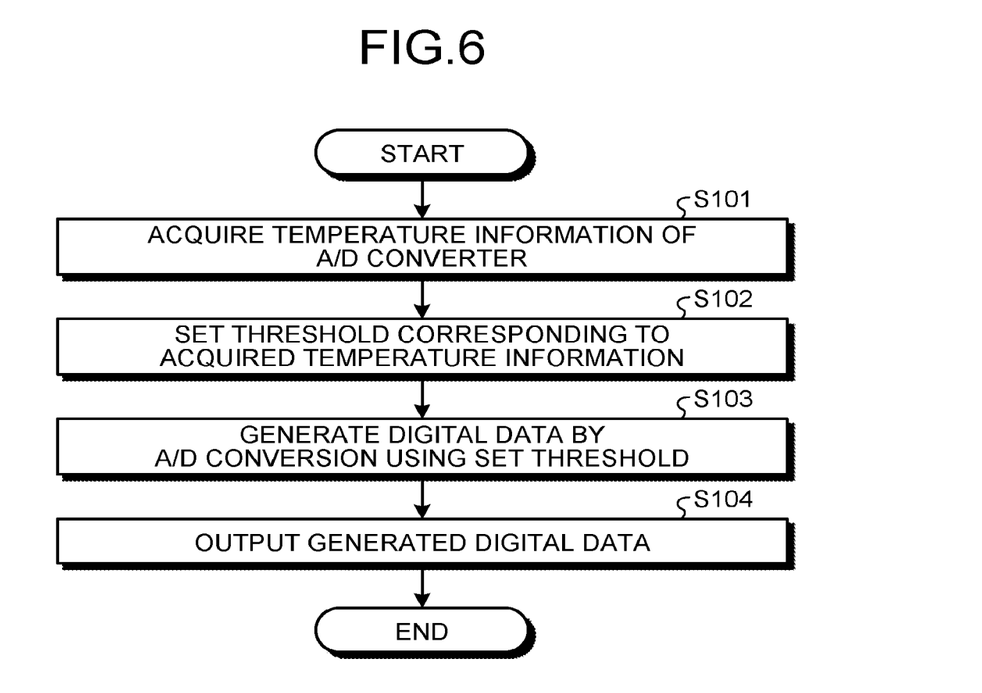
FIG. 6 is a flowchart illustrating an example of a flow of an output control process according to the embodiment.

FIG. 6 is a flowchart illustrating an example of a flow of the output control process according to the first embodiment.

First of all, in the temperature acquiring function 146*a*, the ASIC 146 acquires the temperature information of the A/D converter 145 from the temperature sensor 147 (S101).

In the output controlling function 146*d*, the ASIC 146 sets a threshold for the pulse signal from the analog unit 141 based on the temperature information as described above with reference to FIGS. 3 to 5 (S102).

Note that the process from S101 to S102 need not necessarily be performed every time. When there is no change in the temperature information, the same threshold is set and therefore setting a threshold may be omitted.

In the time information generating function 146*b*, the ASIC 146 acquires time information that is generated by the A/D converter 145 in a state where a threshold is set based on the temperature information. In the count information generating function 146*c*, the ASIC 146 generates count information based on the time information (S103).

Thereafter, in the output controlling function 146*d*, the ASIC 146 outputs digital data on which a temperature compensation is made based on the time information and the count information that are generated, that is, the temperature information of the A/D converter 145 to the console apparatus 20 (S104).

As described above, the temperature compensation according to the first embodiment is realized by changing the threshold, which is set for the analog detection signal for performing A/D conversion, according to the temperature. Specifically, in the output controlling function 146*d*, the ASIC 146 sets a threshold for the pulse signal from the analog unit 141 based on the temperature information. In other words, the ASIC 146 performs the output control such that a change in the output value from the A/D converter 145 that is associated with a temperature change is inhibited and digital data that is compensated based on the temperature information is output from the PET detector 14.

Accordingly, even when there is a significant temperature increase or a temperature decrease in the A/D converter 145 in association with an abrupt change in temperature because of the outside air or high count rate processing, it is possible to minimize fluctuations in energy information.

Second Embodiment

In the first embodiment, the example in which a threshold for energy measurement on the pulse signal from the analog unit 141 is set based on the temperature information is described as an example; however, the threshold is not limited thereto. In the output controlling function 146*d*, the ASIC 146 may set a threshold for the timing of the pulse signal from the analog unit 141 based on the temperature information.

The threshold for the timing of the pulse signal is a threshold for the intensity of the detection signal from the analog unit 141 that is used by the A/D converter 145 to generate time information.

Even with this configuration, the ASIC 146 is able to inhibit a change in the output value from the A/D converter 145 that is associated with a temperature change.

Note that it is possible to combine the technique according to a second embodiment with the technique according to the first embodiment as appropriate. Specifically, the ASIC 146 may be configured to set each of a threshold for energy measurement on the pulse signal from the analog unit 141 and a threshold for generation of time information from the pulse signal based on the temperature information.

Third Embodiment

In each of the embodiments described above, output control of outputting digital data on which a temperature compensation is made by setting a threshold for the pulse signal from the analog unit 141 is exemplified; however, the output control is not limited thereto. In the output controlling function 146d, the ASIC 146 may output digital data on which a temperature compensation is made by controlling operations of the analog unit 141 based on the temperature information.

In the output controlling function 146d, the ASIC 146 determines a voltage to be applied to the SiPM (photoelectric conversion device) of the analog unit 141 based on the temperature information. For example, assume that a table or a relation representing the relationship between the temperature information and the voltage to be applied is determined in advance.

Note that the table or the relation may be one presenting correspondence between temperature information of the SiPM and the voltage to be applied. In this case, the temperature sensor 147 further includes a sensor capable of measuring the temperature of the SiPM.

In an example, when the temperature information is information presenting an environment at a temperature higher than that of the standard temperature environment, in the output controlling function 146d, the ASIC 146 performs output control of applying a voltage lower than that in the case where the temperature information is information presenting the standard temperature environment to the SiPM. In other words, when the temperature information is information presenting an environment at a temperature higher than that of the standard temperature environment, the ASIC 146 lowers the voltage to be applied to the SiPM, thereby transitioning the analog waveform W of the detection signal from the analog unit 141 (for example, downward in FIG. 3 and FIG. 4).

In an example, when the temperature information is information presenting an environment at a temperature lower than that of the standard temperature environment, in the output controlling function 146d, the ASIC 146 performs output control of applying a voltage higher than that in the case where the temperature information is information presenting the standard temperature environment to the SiPM. In other words, when the temperature information is information presenting an environment at a temperature lower than that of the standard temperature environment, the ASIC 146 increases the voltage to be applied to the SiPM, thereby transitioning the analog waveform W of the detection signal from the analog unit 141 (for example, upward in FIG. 3 and FIG. 5).

Also with this configuration, the ASIC 146 is able to inhibit a change in the output value from the PET detector 14 that is associated with a temperature change of the A/D converter 145.

Note that it is possible to combine the technique according to a third embodiment with the technique according to each of the above-described embodiments as appropriate. For example, the ASIC 146 may be configured to set a threshold for the pulse signal from the analog unit 141 and determine a voltage to be applied to the SiPM based on the temperature information.

Fourth Embodiment

In the output controlling function 146d according to a fourth embodiment, the ASIC 146 corrects time information (digital data) that is generated by the time information generating function 146b based on the temperature information. The ASIC 146 the outputs the time information on which the temperature correction is made to the console apparatus 20.

Also with this configuration, the ASIC 146 is able to inhibit a change in the digital data from the PET detector 14 that is associated with a temperature change of the A/D converter 145. Note that it is possible to combine the technique according to the fourth embodiment with the technique according to each of the above-described embodiments.

Fifth Embodiment

In the output controlling function 146d according to a fifth embodiment, the ASIC 146 corrects the count information (digital data) that is generated by the count information generating function 146c based on the temperature information. The ASIC 146 outputs the time information on which the temperature compensation is made to the console apparatus 20.

Also with this configuration, the ASIC 146 is able to inhibit a change in the digital data from the PET detector 14 that is associated with a temperature change of the A/D converter 145. It is possible to combine the technique according to the firth embodiment with the technique according to each of the above-described embodiments.

Sixth Embodiment

In the output controlling function 146d according to a sixth embodiment, the ASIC 146 outputs a command making an instruction for temperature information or temperature compensation to the console apparatus 20 together with the generated digital data. The command making an instruction for temperature compensation is generated based on the temperature information.

The console apparatus 20 according to the sixth embodiment corrects the digital data from the PET detector 14 based on the command making an instruction for temperature information or temperature compensation from the PET detector 14. Specifically, in the controlling function 24a, the processing circuitry 24 controls the PET detector 14 to collect time information and coefficient information (digital data), makes a temperature compensation on the collected digital data, and stores the digital data after the temperature compensation in the memory 23. The processing circuitry 24 that realizes the controlling function 24a is an example of a controller.

Also with this configuration, in the PET apparatus 100, it is possible to inhibit the effect of a change of the digital data from the PET detector 14 that is associated with the temperature change of the A/D converter 145. Note that it is possible to appropriately combine the technique according to the sixth embodiment with the technique according to each of the above-described embodiments.

Seventh Embodiment

In the output controlling function 146d according to a seventh embodiment, the ASIC 146 controls a temperature controller that is mounted on the A/D converter 145 based on the temperature information.

The temperature controller is a heater or a cooler that is configured to be able to adjust the temperature of the A/D converter 145 or a combination of the heater and the cooler. For example, a fan is usable as the cooler.

In an example, when the temperature information is information presenting an environment at a temperature higher than that of the standard temperature environment, in the output controlling function 146d, the ASIC 146 turns the cooler on.

In an example, when the temperature information is information presenting an environment at a temperature higher than that of the standard temperature environment, in the output controlling function 146d, the ASIC 146 causes the fan to turn at a rotation speed higher than that in the case where the temperature information is information presenting the standard temperature environment.

In an example, when the temperature information is information presenting an environment at a temperature higher than that of the standard temperature environment, in the output controlling function 146d, the ASIC 146 turns the heater off.

In an example, when the temperature information is information presenting an environment at a temperature lower than that of the standard temperature environment, in the output controlling function 146d, the ASIC 146 turns the cooler off.

In an example, when the temperature information is information presenting an environment at a temperature higher than that of the standard temperature environment, in the output controlling function 146d, the ASIC 146 causes the fan to turn at a rotation speed lower than that in the case where the temperature information is information presenting the standard temperature environment.

In an example, when the temperature information is information presenting an environment at a temperature lower than that of the standard temperature environment, in the output controlling function 146d, the ASIC 146 turns the heater on.

Also with these configurations, the ASIC 146 is able to inhibit a change in the output value from the PET detector 14 that is associated with a temperature change of the A/D converter 145. It is possible to combine the technique according to the seventh embodiment with the technique of each of the above-described embodiments.

Note that the temperature compensation method according to the embodiment may be realized by an apparatus independent of the PET apparatus 100, such as a computer including a processor and a memory as hardware resources. In this case, the processor that is mounted on the computer executes a program that is read from the ROM, or the like, and is loaded into the RAM, thereby realizing the temperature compensation method according to the embodiment.

The temperature compensation method according to each of the embodiments may be realized in a photon counting computed tomography (PCCT) apparatus. In this case, a processor that is mounted on the PCCT apparatus executes a program that is read from a ROM, or the like, and is loaded into a RAM, thereby realizing the temperature compensation method according to each of the embodiments.

For example, there are various types of X-ray CT apparatuses including a third-generation CT and a fourth-generation CT and any type is applicable to each of the embodiments. The third-generation CT is a rotate/rotate-type in which an X-ray-tube and a detector rotate as a unit around a subject. In the fourth-generation CT, the fourth-generation CT is a stationary/rotate-type in which a large number of X-ray detection devices that are arrayed in a ring-like form are fixed and only an X-ray tube rotates around a subject.

The word "processor" used in the description given above refers to, for example, circuitry, such as a CPU, a GPU, an ASIC, or a programmable logic device (PLD). The PLD covers a SPLD, a CPLD, and a FPGA. The processor reads programs that are saved in storage circuitry and executes the programs, thereby implementing the functions. The storage circuitry in which the programs are saved is a computer-readable non-temporary recording medium. Instead of saving the programs in the storage circuitry, the programs may be directly installed in the circuitry of the processor. In this case, the processor reads and executes the programs that are installed in the circuitry, thereby implementing the functions. Without executing the programs, the functions corresponding to the programs may be implemented by a combination of sets of logic circuitry. Note that each processor of the embodiments is not limited to the case where each processor is configured as a single set of circuitry, and a plurality of independent sets of circuitry may be combined to configure a single processor to implement the functions. Furthermore, the components in FIG. 1 or FIG. 2 may be integrated into one processor to implement functions thereof.

According to at least one of the embodiments described above, tie is possible to appropriately compensate an effect of a temperature change in a radiation detector.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

With respect to the above-described embodiments, the following appendants are disclosed as one aspect and selective characteristics of the invention.

(Appendant 1)

A radiation detector including:
- a sensor unit that outputs a pulse signal based on incidence of radiation;
- an A/D converter that generates digital data by performing A/D conversion on the pulse signal;
- an acquisition unit that acquires temperature information of the A/D converter; and
- an output controller that outputs digital data that is compensated based on the temperature information.

(Appendant 2)

A nuclear medicine diagnostic apparatus including:
- a radiation detector including
  - a sensor unit that outputs a pulse signal based on incidence of radiation,
  - an A/D converter that generates digital data by performing A/D conversion on the pulse signal,
  - an acquisition unit that acquires temperature information of the A/D converter, and
  - an output controller that outputs digital data; and a controller that makes a temperature compensation on the digital data from the radiation detector based on the temperature information.

(Appendant 3)

The output controller may set a threshold for the pulse signal based on the temperature information.

(Appendant 4)

The threshold may be a threshold for energy measurement on the pulse signal.

(Appendant 5)

The threshold may be a threshold for timing of the pulse signal.

(Appendant 6)

The output controller may correct the digital data based on the temperature information.

(Appendant 7)

The digital data may be at least any one of time information and count information.

(Appendant 8)

The output controller may determine a voltage to be applied to the sensor unit based on the temperature information.

(Appendant 9)

The acquisition unit may further acquire temperature information of the sensor unit.

The output controller may determine the voltage to be applied to the sensor unit further based on the temperature information of the sensor unit.

(Appendant 10)

The radiation detector may further include a temperature controller that controls a temperature of the A/D converter.

The output controller may control an operation of the temperature controller based on the temperature information.

What is claimed is:

1. A radiation detector comprising:
a sensor that outputs a pulse signal based on incidence of radiation;
an A/D converter that generates digital data by performing A/D conversion on the pulse signal; and
processing circuitry that acquires temperature information of the A/D converter and that outputs digital data that is compensated based on the temperature information.

2. The radiation detector according to claim 1, wherein the processing circuitry sets a threshold for the pulse signal based on the temperature information.

3. The radiation detector according to claim 2, wherein the threshold is a threshold for energy measurement on the pulse signal.

4. The radiation detector according to claim 2, wherein the threshold is a threshold for timing of the pulse signal.

5. The radiation detector according to claim 1, wherein the processing circuitry corrects the digital data based on the temperature information.

6. The radiation detector according to claim 5, wherein the digital data is at least one of time information and count information.

7. The radiation detector according to claim 1, wherein the processing circuitry determines a voltage to be applied to the sensor unit based on the temperature information.

8. The radiation detector according to claim 7, wherein
the processing circuitry further acquires temperature information of the sensor unit, and
determines the voltage to be applied to the sensor unit based on the temperature information of the sensor unit.

9. The radiation detector according to claim 1, further comprising a temperature controller that controls a temperature of the A/D converter, and
the processing circuitry controls an operation of the temperature controller based on the temperature information.

10. A nuclear medicine diagnostic apparatus comprising:
a radiation detector including
a sensor that outputs a pulse signal based on incidence of radiation,
an A/D converter that generates digital data by performing A/D conversion on the pulse signal, and
processing circuitry that acquires temperature information of the A/D converter and that outputs the digital data; and
a processor that makes a temperature compensation on the digital data from the radiation detector based on the temperature information.

* * * * *